United States Patent
Bernhardt et al.

(10) Patent No.: US 11,331,065 B2
(45) Date of Patent: May 17, 2022

(54) X-RAY DEVICE AND A METHOD FOR OPERATING AN X-RAY DEVICE WHEN CARRYING OUT AN X-RAY EXAMINATION

(71) Applicant: Siemens Healthcare GmbH, Erlangen (DE)

(72) Inventors: Philipp Bernhardt, Forchheim (DE); Andreas Berting, Schlüchtern (DE); Stefan Böhm, Oberasbach (DE); Boris Stowasser, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 127 days.

(21) Appl. No.: 16/782,173

(22) Filed: Feb. 5, 2020

(65) Prior Publication Data
US 2020/0268336 A1 Aug. 27, 2020

(30) Foreign Application Priority Data
Feb. 25, 2019 (DE) .......................... 102019202518.8

(51) Int. Cl.
*A61B 6/00* (2006.01)
(52) U.S. Cl.
CPC ................................. *A61B 6/5235* (2013.01)
(58) Field of Classification Search
CPC ..... A61B 6/5235; A61B 6/481; A61B 6/5258; A61B 6/5205; A61B 6/504; A61B 6/52; A61B 6/542; A61B 6/54
See application file for complete search history.

(56) References Cited

U.S. PATENT DOCUMENTS

| | | | | |
|---|---|---|---|---|
| 4,881,124 A | * | 11/1989 | Yokouchi | H04N 5/3205 378/98.2 |
| 2010/0158341 A1 | | 6/2010 | Baumgart | |
| 2013/0077750 A1 | * | 3/2013 | Yabugami | A61B 6/481 378/62 |

FOREIGN PATENT DOCUMENTS

DE 102006037969 A1 2/2008

OTHER PUBLICATIONS

German Office Action for German Application No. 10 2019 202 518.8 dated Oct. 15, 2020.
(Continued)

*Primary Examiner* — David P Porta
*Assistant Examiner* — Mamadou Faye
(74) *Attorney, Agent, or Firm* — Lempia Summerfield Katz LLC

(57) ABSTRACT

A method is provided for operating a medical X-ray device when carrying out an X-ray examination. In order to reduce the duration of the scan for the reliable determination of changes over time in a body region of an examination subject by an X-ray based subtraction method, the method includes recording a plurality of first X-ray images of a body region of an examination subject, wherein the recording of the plurality of first X-ray images ensues at a constant X-ray imaging frequency and a constant X-ray dose for each X-ray image recording. The method further includes generating a mask image, wherein the generation of the mask image includes an averaging of the plurality of first X-ray images; recording of at least one second X-ray image of the body region at a further time after the recording of the plurality of first X-ray images, wherein the recording of the at least one second X-ray image ensues at the same constant X-ray imaging frequency and the same constant X-ray dose for each X-ray image recording as for recording the first X-ray (Continued)

images; and generating a total image at least as a function of the mask image and of the at least one second X-ray image.

15 Claims, 6 Drawing Sheets

(56) References Cited

OTHER PUBLICATIONS

Rath, M. et al: "Digital Radiography"; RöFo Advances in X-rays and Imaging; vol. 140; No. 3; Georg Thieme Publishing House Stuttgar-New York; 1984; pp. 243-250 with English translation.

* cited by examiner

X-RAY DEVICE AND A METHOD FOR OPERATING AN X-RAY DEVICE WHEN CARRYING OUT AN X-RAY EXAMINATION

The present patent document claims the benefit of German Patent Application No. 10 2019 202 518.8, filed Feb. 25, 2019, which is hereby incorporated by reference.

TECHNICAL FIELD

The disclosure relates to a method for operating a medical X-ray device when carrying out an X-ray examination. A second aspect of the disclosure relates to a medical X-ray device.

BACKGROUND

It is known from the prior art that for recording changes over time in a body region of an examination subject, (e.g., a movement in the body region), X-ray based subtraction methods or pathfinder methods may be used. A change over time in the body region of the examination subject may include a spreading movement of a contrast agent in a vascular system and/or a movement of a catheter.

In these X-ray based subtraction methods, at least two X-ray images may be recorded in chronological sequence, which show the same body region. The two X-ray images are subtracted one from the other, wherein the components in the X-ray images that are irrelevant and/or disruptive for a therapy and/or diagnosis, and which in particular remain unchanged over time, are reduced.

In methods such as digital subtraction angiography (DSA), a distinction may be made between two imaging phases.

In a first phase, at least one X-ray image may be recorded with optimum image quality, e.g., with a maximum X-ray dose. In a second phase, which is chronologically later than the first phase, at least one second X-ray image may be recorded, wherein a change in the body region of the examination subject that has been examined has taken place at this time. To record this change over time in the body region, (e.g., a spreading movement of the contrast agent and/or a movement of the catheter), a plurality of second X-ray images may be recorded one after the other in a short time sequence. To facilitate this, a different X-ray imaging frequency and/or X-ray dose than in the first phase may be used. As a result, it is necessary to change a detector mode and/or a tube current, as a result of which the duration of the scan as a whole is increased.

The change over time in the body region may subsequently be made visible through subtraction of an X-ray image from the first phase and of one of the second X-ray images from the second phase.

It is further known from the prior art that an image noise variance in the first X-ray image and an image noise variance in the second X-ray image is added in the subtraction to an image noise variance in a differential image. For this reason, a maximum X-ray dose may be selected for the recording of the first X-ray image because, as a result thereof, the image noise variance is reduced in comparison with the intensity in the first X-ray image. As a result, a higher image quality may be achieved in the first X-ray image, and hence likewise in a difference image.

SUMMARY AND DESCRIPTION

The object underlying the disclosure is to reduce the duration of a scan for the reliable recording of changes over time in a body region of an examination subject by an X-ray based subtraction method.

The scope of the present disclosure is defined solely by the appended claims and is not affected to any degree by the statements within this summary. The present embodiments may obviate one or more of the drawbacks or limitations in the related art.

According to a first variant of a method for operating a medical X-ray device when carrying out an X-ray examination, provision is made for a plurality of first X-ray images of a body region of an examination subject to be recorded, wherein the recording of the plurality of first X-ray images ensues at a constant X-ray imaging frequency and a constant X-ray dose for each X-ray image recording. Furthermore, a mask image is generated, wherein the generation of the mask image includes an averaging of the plurality of first X-ray images. Furthermore, at least one second X-ray image of the body region is recorded at a further time after the recording of the plurality of first X-ray images, wherein the recording of the at least one second X-ray image ensues at the same constant X-ray imaging frequency and the same constant X-ray dose for each X-ray image recording as that used to record the first X-ray images. Furthermore, a total image is generated at least as a function of the mask image and of the at least one second X-ray image.

The recording of the plurality of first X-ray images may be perceived in particular as the first phase of the X-ray examination. The plurality of first X-ray images are recorded at a constant X-ray imaging frequency and a constant X-ray dose for each X-ray image recording, wherein the constant X-ray imaging frequency may be referred to as a constant recording rate of a detector. A constant X-ray dose refers here in particular to a constant X-ray dose over the first phase of the X-ray examination for each X-ray image recording. Through the constant X-ray imaging frequency and the constant X-ray dose for each X-ray image recording in the first phase of the X-ray examination, changing the detector mode and/or tube current in the first phase is advantageously avoided. As a result, a comparable intensity and a comparable variation in noise is achieved between the individual X-ray images from the first phase.

When generating the mask image, the averaging of the plurality of first X-ray images may take place during the first phase of the X-ray examination.

This averaging may ensue in an iterative manner. After the recording of at least two first X-ray images, an averaging of the two first X-ray images to form an intermediate averaging image may take place. After the recording of a further first X-ray image, the further first X-ray image, (e.g., weighted), may be averaged with the intermediate averaging image. The weighted averaging makes it possible to provide that, in each act of the iterative averaging, the individual first X-ray images are incorporated with equal weighting into the following intermediate averaging image. In particular, after the recording of a final first X-ray image and the weighted averaging of the final first X-ray image with the intermediate averaging image, the mask image is generated from the intermediate averaging image. This may be advantageous in the case of a limited X-ray image memory, (e.g., a memory unit), because it is only the intermediate averaging image and the at least one further first X-ray image that have to be preserved in the X-ray image memory. Advantageously, here the final first X-ray image is retained in the X-ray image memory in addition to the intermediate averaging image.

In particular, the generation of the mask image, which includes an averaging of the plurality of first X-ray images that have been recorded at a constant X-ray dose, may be perceived as an effective increase of the X-ray dose in the mask image. As a result, a higher intensity and less image noise variance in comparison with the individual first X-ray images are achieved, wherein the improvement in the intensity and the reduction in the image noise variance is achieved as with a comparatively higher X-ray dose equivalent than in the first phase of the X-ray examination. The improvement in intensity and the reduction in the image noise variance in an X-ray image may be perceived in particular as an improvement in the image quality of the X-ray image.

The recording of at least one second X-ray image of the body region at a further time after the recording of the plurality of first X-ray images may be perceived as a second phase of the X-ray examination that takes place at a later time than the first phase of the X-ray examination. As a result of the fact that, in this second phase, the recording of the at least one second X-ray image ensues at the same constant X-ray imaging frequency and the same constant X-ray dose for each X-ray image recording as for recording the first X-ray images during the first phase of the X-ray imaging, changing of the tube current and/or of the detector mode is advantageously avoided. Here, the detector mode may include a sensitivity setting to an X-ray dose and/or an X-ray imaging frequency. This allows a seamless transition between the first and second phase of the X-ray examination. As a result of the fact that the X-ray images are recorded at the same constant X-ray imaging frequency and the same constant X-ray dose during the first and second phase, a comparable intensity and a comparable image noise variance between the individual X-ray images from the first and the second phase is advantageously achieved.

Due to the fact that the generation of the total image occurs at least as a function of the mask image and of the at least one further X-ray image, the improved image quality of the mask image in comparison with the image quality of the at least one second X-ray image may contribute to the reduction in additional image noise during the generation of the total image. As a result, although each of the plurality of first X-ray images individually has a poorer image quality than the mask image averaged therefrom, an image quality of the total image that corresponds to a higher X-ray dose equivalent for the mask image may be achieved. This means that, despite a reduced duration of the scan, an image quality of the total image that is at least equal to an image quality achieved with the X-ray dose equivalent for the averaged mask image from the first phase may be achieved.

In a further advantageous embodiment, in the generation of the total image, the mask image and the at least one second X-ray image are subtracted one from the other. A difference image that results therefrom contains in particular a representation of the change over time in the body region of the examination subject that has taken place after the first phase of the X-ray examination, that is, after the recording of the plurality of first X-ray images. Through the subtraction, advantageously all the components that remain unchanged over time between the first and second phase of the X-ray examination may be removed from the difference image.

In a further advantageous embodiment, the generation of the total image may additionally ensue as a function of a second subsequent image, wherein a first subsequent image is generated from at least one of the first X-ray images and wherein the second subsequent image is acquired through an adaptive averaging of the first subsequent image and at least as a function of the at least one second X-ray image. Here, the adaptive averaging may include an, in particular weighted, averaging wherein the first subsequent image in particular may be acquired from at least one of the first X-ray images. For example, the first subsequent image may be generated by averaging a plurality of first X-ray images. Advantageously, the adaptive averaging occurs to generate the second subsequent image as a function of the at least one second X-ray image, wherein the at least one second X-ray image is recorded in the second phase of the X-ray examination and the change over time in the body region of the examination subject may be represented at least partly.

In a further advantageous embodiment, the adaptive averaging, (e.g., for generating the second subsequent image), includes an averaging of the first subsequent image and of the at least one second X-ray image. Here, a weighted averaging between the first subsequent image and the at least one second X-ray image may be particularly advantageous because, as a result thereof, an increase in the identifiability of the change over time in the body region of the examination subject may be achieved in the second subsequent image in comparison with a background of the at least one second X-ray image. Furthermore, an improvement in the image quality may be achieved through the adaptive averaging of the first subsequent image with the at least one second X-ray image, in particular, when the first subsequent image has been generated by averaging a plurality of first X-ray images.

In a further advantageous embodiment, an averaging value that is dependent on a degree of deviation for the adaptive averaging of the first subsequent image and of the at least one second X-ray image may be determined, the degree of deviation being determined from a deviation between at least one of the first X-ray images and the at least one second X-ray image. Here, it is particularly advantageous that the plurality of first X-ray images and the at least one second X-ray image are recorded at the same constant X-ray imaging frequency and the same constant X-ray dose for each X-ray image recording. This allows a direct reconciliation between the first X-ray images and the at least one second X-ray image. This allows, in particular, the determination of a deviation between the at least one first X-ray image and the at least one second X-ray image. This deviation may include information that shows the change over time in the body region of the examination subject between the first and the second phase of the X-ray examination, due for example, to a spreading movement of a contrast agent and/or a movement of a catheter. As a function of this deviation, a degree of deviation may be determined, which provides a weighting for the adaptive averaging of the first subsequent image and of the at least one second X-ray image. In particular, the degree of deviation and consequently also the weighting for the adaptive averaging in sub-areas of the images to be averaged may be different.

In a further advantageous embodiment, an averaging value for the adaptive averaging of the first subsequent image and of the at least one second X-ray image may be determined from a degree of deviation, wherein the degree of deviation is determined by a degree of deviation between the first subsequent image and the at least one second X-ray image. The determination of the degree of deviation by a deviation between the first subsequent image and the at least one second X-ray image is particularly advantageous, because the better image quality of the first subsequent image may be used, for example, in comparison with the at least one second X-ray image. For example, the first subsequent image may be generated by averaging a plurality of first X-ray images, as a result of which a better image quality is achieved than in the individual first X-ray images. Here, the degree of deviation may provide a weighting for the adaptive averaging of the first subsequent image and of the at least one second X-ray image. In particular, sub-areas of the at least one second X-ray image that show a slight deviation from the first subsequent image may be averaged with a lower weighting than corresponding regions of the first subsequent image. As a result, the image quality of the second subsequent image may be improved. In particular, in the adaptive averaging of the first subsequent image, a plurality of second X-ray images may be averaged, as a result of which a change over time in the body region of the examination subject in the second subsequent image may be accumulated across the times for the recordings of the plurality of second X-ray images.

In a further advantageous embodiment, an averaging value that is dependent on a degree of deviation may be determined, wherein a plurality of first X-ray images are averaged to form a first intermediate averaging image and an identical number of second X-ray images are averaged to form a second intermediate averaging image. The first subsequent image is formed by the first intermediate averaging image. Additionally, the degree of deviation is determined by a deviation between the first subsequent image and the second intermediate averaging image. Further, the adaptive averaging includes an averaging of the first subsequent image and of the second intermediate averaging image.

As a result, the plurality of first X-ray images and the plurality of second X-ray images may be recorded at an X-ray imaging frequency and an X-ray dose for each X-ray image recording that allows the duration of the scan as a whole to be shortened yet reduces the image quality of the individual X-ray images in the first and second phase of the X-ray examination. Here, by averaging a plurality of first X-ray images to form the first intermediate averaging image and averaging an identical number of second X-ray images to form the second intermediate averaging image, a better image quality compared with the individual X-ray images may be achieved in the first and the second intermediate averaging image and consequently an image quality that corresponds with a better X-ray dose equivalent. Through the averaging of an identical number of second X-ray images for generating the second intermediate averaging image, as with the first intermediate averaging image, the possibility of a direct reconciliation between the first and the second intermediate averaging image is maintained due to a comparable intensity and a comparable variation in image noise. In particular, a plurality of second intermediate averaging images may also be generated by the recording of further second X-ray images, wherein an accumulation of the change over time in the body region of the examination subject over the times of the recordings of the plurality of second X-ray images is facilitated.

In a further advantageous embodiment, during the generation of the total image, the mask image and the second subsequent image are subtracted one from the other. As a result, the improved image quality and/or the improvement in individual sub-areas in the second subsequent image that show the change over time in the body region of the examination subject may be transferred to the total image by the adaptive averaging used for generating the second subsequent image.

In a further advantageous embodiment, only a part of the first X-ray images is averaged to generate the mask image. As a result, a dynamic adjustment of the X-ray dose equivalent for the averaged image may be facilitated. Furthermore, by excluding individual first X-ray images from the averaging to form the mask image, a reduction in image artefacts may be achieved insofar as the artefacts are contained only in the excluded individual first X-ray images.

In a further advantageous embodiment, a plurality of second X-ray images may be recorded, with a plurality of total images being generated, each of the plurality of total images being generated by subtraction of the mask image from one of the plurality of second X-ray images. As a result, the creation of a scene, of a film and/or of a film loop, for example, is advantageously facilitated. This scene may show the course over time of the movement in the body region of the examination subject. Through the subtraction of the mask image from each of the plurality of second X-ray images for generating a plurality of total images, the state of the change in the body region of the examination subject at the time of recording the respective second X-ray image is advantageously preserved in each of the plurality of total images. In particular, each of the plurality of total images shows the change over time in the body region of the examination subject at a different time that corresponds with the respective time of recording of the relevant second X-ray image.

In a further advantageous embodiment, the number of the plurality of first X-ray images that are averaged to generate the mask image may be determined by the number of the plurality of second X-ray images. This may be advantageous for a better image quality of the plurality of total images. The image quality Q of an X-ray image may be seen as a parameter that is indirectly proportional to the image noise variance. During the generation of the total image by subtraction of the mask image from one of the second X-ray images, the normalized image quality $Q/Q_0$ of the total image may be expressed as a function of the number N1 of the plurality of first X-ray images that have been averaged to generate the mask image, as shown in equation (1) below:

$$\frac{Q}{Q_0} = \frac{N1}{N1+1}. \qquad (1)$$

A normalized X-ray dose $D/D_0$ for the scene formed in particular from the plurality of total images may be expressed as follows in equation (2):

$$\frac{D}{D_0} = N1 + N2. \qquad (2)$$

Here, N2 describes the number of second X-ray images. A maximum for the relationship between the normalized image quality and the normalized X-ray dose for the scene may be achieved for an averaging of $N1=\sqrt{N2}$ first X-ray images to form the mask image. As a result, a maximum image quality of each of the plurality of total images for a specific constant X-ray dose for each X-ray image recording and a specific number N2 of second X-ray images may be achieved.

In a further advantageous embodiment, the X-ray device includes an X-ray unit and a detector wherein, after and/or before the recording of at least one second X-ray image, at least one dark image is recorded without exposure of the detector. For recording the plurality of first and the plurality of second X-ray images, an X-ray imaging frequency may be selected that minimizes the recording time for recording the plurality of first X-ray images at a given X-ray dose and/or number of the plurality of first X-ray images. The X-ray imaging frequency may be higher than is necessary for a reliable representation of the course over time of the change in the body region of the examination subject, for example, for the spreading movement of a contrast agent and/or for the movement of a catheter. By recording at least one dark image before and/or after recording at least one second X-ray image, the frequency for the exposure of the detector may be reduced during the recording of the second X-ray images. As a result, the X-ray imaging frequency of the detector may remain unchanged in comparison with the first phase, wherein the at least one dark image is not included in the second X-ray images and, due to the lack of exposure, does not contribute to the X-ray dose in the second phase. By recording the at least one dark image before and/or after recording the at least one second X-ray image, the period of time between the recording of the plurality of second X-ray images may be lengthened. Advantageously, the X-ray imaging frequency for the second X-ray images, which differs from the X-ray imaging frequency of the detector, (e.g., due to the recording of at least one dark image before and/or after recording at least one second X-ray image), may as a result thereof be adjusted to a movement rate in the change over time in the body region of the examination subject.

In a further advantageous embodiment, by the at least one dark image, detector information may be determined, wherein at least one of the plurality of total images is generated considering the detector information. The detector information determined by the at least one dark image may include noise information and/or information about afterglow characteristics of the detector. Furthermore, when recording a plurality of dark images in chronological order, a course over time of decay characteristics and/or afterglow characteristics of the detector is acquired and assigned to the detector information. When generating at least one of the plurality of total images, the detector information may be considered, wherein the detector information may contribute in particular to the improvement in the image quality and/or to a reduction in the variation in image noise. Advantageously, the at least one dark image may be recorded without any additional measurement work and without increasing the X-ray dose and may be used to determine the detector information.

Furthermore, a medical X-ray device is proposed, which is embodied to perform a method for operating a medical X-ray device when carrying out an X-ray examination. Furthermore, the X-ray device is embodied to record a plurality of first X-ray images of a body region of an examination subject, wherein the recording of the plurality of first X-ray images ensues at a constant X-ray imaging frequency and a constant X-ray dose for each X-ray image recording. Furthermore, the X-ray image is embodied to generate a mask image, wherein the generation of the mask image includes an averaging of the plurality of first X-ray images. Furthermore, the X-ray device is embodied to record at least one further X-ray image of the body region at a further time after the recording of the plurality of first X-ray images, wherein the recording of the at least one second X-ray image ensues at the same constant X-ray imaging frequency and the same constant X-ray dose for each X-ray image recording as for recording the first X-ray images. Furthermore, the X-ray device is embodied to generate an overall image at least as a function of the mask image and of the at least one second X-ray image.

Furthermore, a processing unit, (e.g., a microprocessor), is proposed which is embodied to process information and/or data and/or signals from the medical X-ray device and/or further components. Furthermore, the processing unit is embodied to send control commands to the X-ray device and/or components thereof and/or further components.

The medical X-ray device may include a display unit, (e.g., a display and/or monitor), which is configured to display information and/or graphic representations of information relating to the X-ray device and/or to further components.

The advantages of the proposed X-ray device correspond to the advantages of the proposed method for operating a medical X-ray device when carrying out an X-ray examination. Features, advantages, or alternative embodiments mentioned here may equally well be applied to the other claimed subjects and vice versa.

Furthermore, a computer program product is proposed, which includes a program and may be loaded directly into a memory of a programmable computation unit and includes programming code or modules, such as libraries and auxiliary functions in order to carry out a method for operating a medical X-ray device when carrying out an X-ray examination when the computer program product is run. The computer program product may include software with a source code that still has to be compiled and bound or merely interpreted, or an executable software code, which only has to be loaded into the processing unit for execution. By the computer program product, the method for operating a medical X-ray device when carrying out an X-ray examination may be carried out quickly, in an identically repeatable manner, and robustly. The computer program product is configured such that it may carry out the method acts by the processing unit. The processing unit has certain prerequisites, such as an appropriate main memory, an appropriate graphics card, or an appropriate logic unit, such that the respective method acts may be carried out efficiently.

The computer program product is, for example, stored on a computer-readable medium or deposited on a network or server from where the computer program product may be loaded into the processor of a processing unit, which may be directly connected to the processing unit or embodied as part of the processing unit. Furthermore, control information for the computer program product may be stored on an electronically readable data carrier. The control information on the electronically readable data carrier may be embodied such that, when the data carrier is used in a processing unit, it carries out the method. Examples of electronically readable data carriers are a DVD, a magnetic tape or a USB stick on which electronically readable control information, (e.g., software), is stored. When this control information is read by the data carrier and stored in a processing unit, all the embodiments of the method described previously may be carried out. The disclosure may therefore also take as its point of departure the computer-readable medium and/or the electronically readable data carrier.

BRIEF DESCRIPTION OF THE DRAWINGS

Exemplary embodiments of the disclosure are shown in the drawings and are described in further detail hereinafter. In different figures the same features are denoted by the same reference signs.

DETAILED DESCRIPTION

Figure 1:
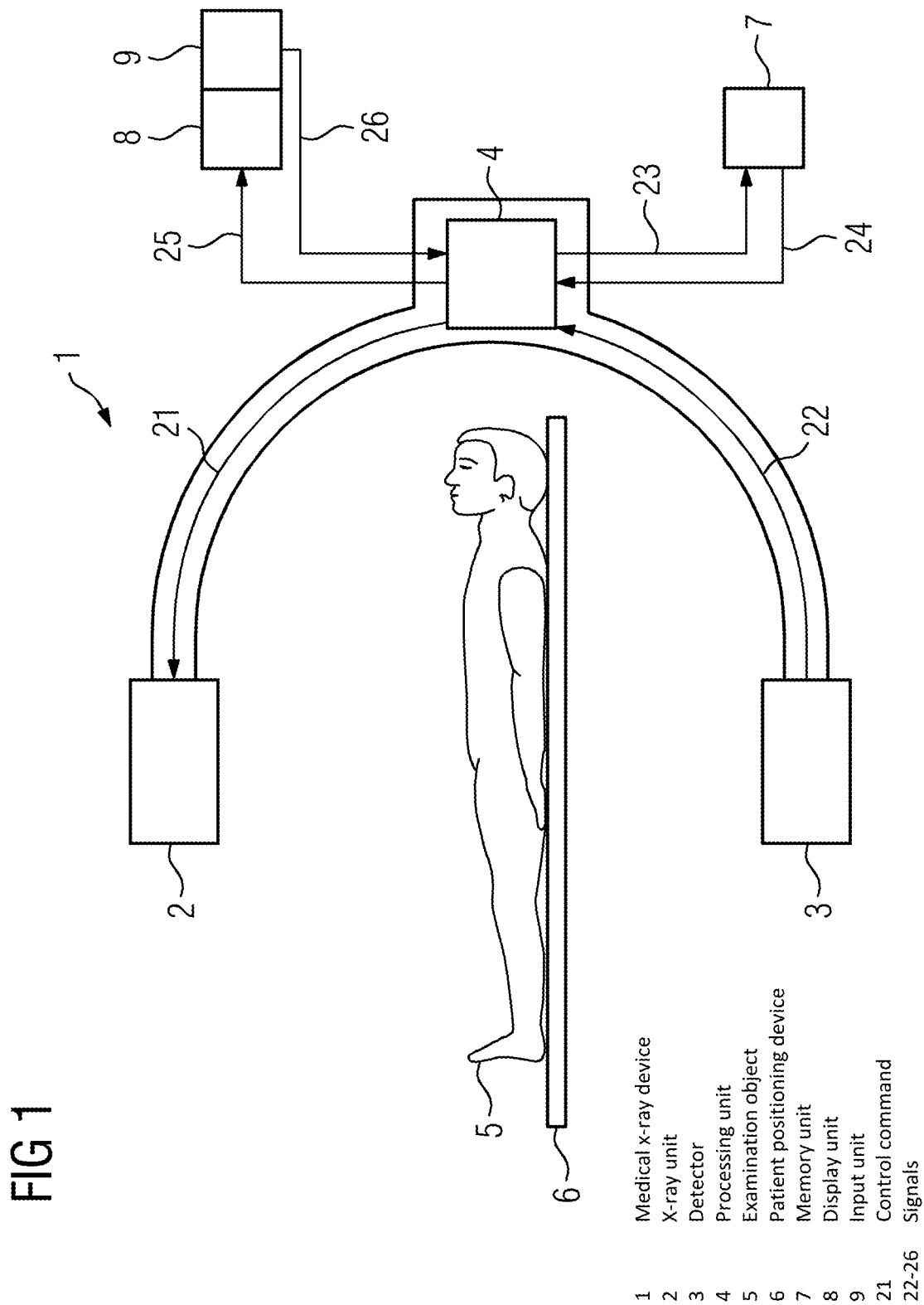
FIG. 1 depicts an example of a schematic representation of a medical X-ray device.

In one embodiment, shown by way of example in FIG. 1, a medical X-ray device 1 for examining a body region of an examination subject 5 includes an X-ray unit 2, a detector 3, and a processing unit 4. In particular, the X-ray device 1 may include a C-arm X-ray device. Furthermore, the examination subject 5 may advantageously be arranged on a patient positioning device 6.

In particular, the processing unit 4 is embodied to transmit a control command 21 to the X-ray unit 2, by which an emission of X-rays, (e.g., chronologically pulsed), may be triggered and/or controlled. Furthermore, the processing unit 4 is embodied to receive and process a signal 22 from the detector. In particular, the processing of a signal 22 from the detector may also include storage and/or intermediate storage inside the processing unit 4 and/or a memory unit 7 connected thereto. If a signal 22 from the detector 3 is stored in a memory unit 7, the processing unit 4 transmits a signal 23 to the memory unit 7. If the at least one signal 23, (e.g., stored in the memory unit 7), is required for a method act in the processing unit 4, the memory unit 7 is then configured to transmit a signal 24 to the processing unit 4. Furthermore, the processing unit 4 may transmit a signal 25 to a display unit 8, which may include a display and/or monitor. On the display unit 8, a representation of at least one total image and/or a second X-ray image, (e.g., a most recently recorded image), may ensue, wherein the representation of a plurality of different images may ensue, (e.g., side by side and/or in superimposed form). Furthermore, the display unit 8 may be embodied to display a scene, for example, a film and/or a film loop that includes a plurality of total images.

Furthermore, the display unit 8 may include an input unit 9, wherein the input unit 9 may transmit a control signal 26 to the processing unit. In particular, the input unit 9 may be incorporated into the display unit 8, as for example, in a capacitive display. Through the input unit 9, a control of the X-ray examination may ensue, for example, through the input of the X-ray dose and/or of the X-ray imaging frequency and/or of an X-ray imaging protocol and/or of the number of the plurality of first X-ray images and/or of the number of the plurality of second X-ray images.

Figure 2:
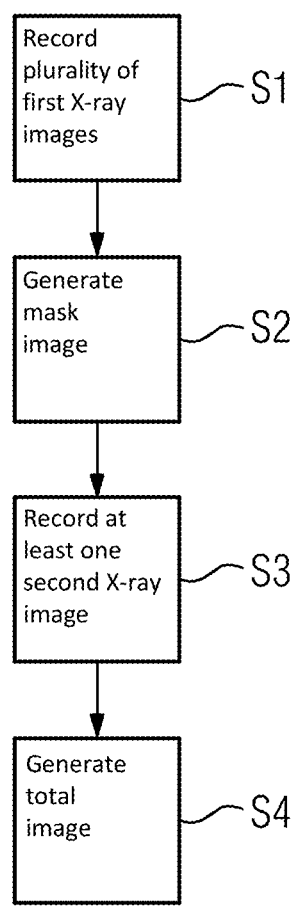
FIG. 2 depicts an example of a schematic representation of the method acts for operating a medical X-ray device when carrying out an X-ray examination.

FIG. 2 depicts a schematic representation of the method acts for operating a medical X-ray device 1 when carrying out an X-ray examination. In a first act S1, a plurality of first X-ray images 11 of a body region of an examination subject 5 are recorded, wherein the recording of the plurality of first X-ray images 11 ensues at a constant X-ray imaging frequency and a constant X-ray dose for each X-ray image recording. In a second act S2, which may even start during the recording of at least one further first X-ray image, a mask image 13 is generated, with the generation of the mask image 13 including an averaging of the plurality of first X-ray images 11. In a third act S3, at least one second X-ray image 12 of the body region is recorded at a further time after the recording of the plurality of first X-ray images 11, wherein the recording of the at least one second X-ray image 12 ensues at the same constant X-ray imaging frequency and the same constant X-ray dose for each X-ray image recording as for recording the first X-ray images 11. In a fourth act S4, a total image 16 is generated at least as a function of the mask image 13 and of the at least one second X-ray image 12. In particular, in act S2, only a part of the first X-ray images 11 may be averaged to form the mask image 13. This may be advantageous in particular for a dynamic adjustment of the X-ray dose equivalent of the mask image 13.

Figure 3:
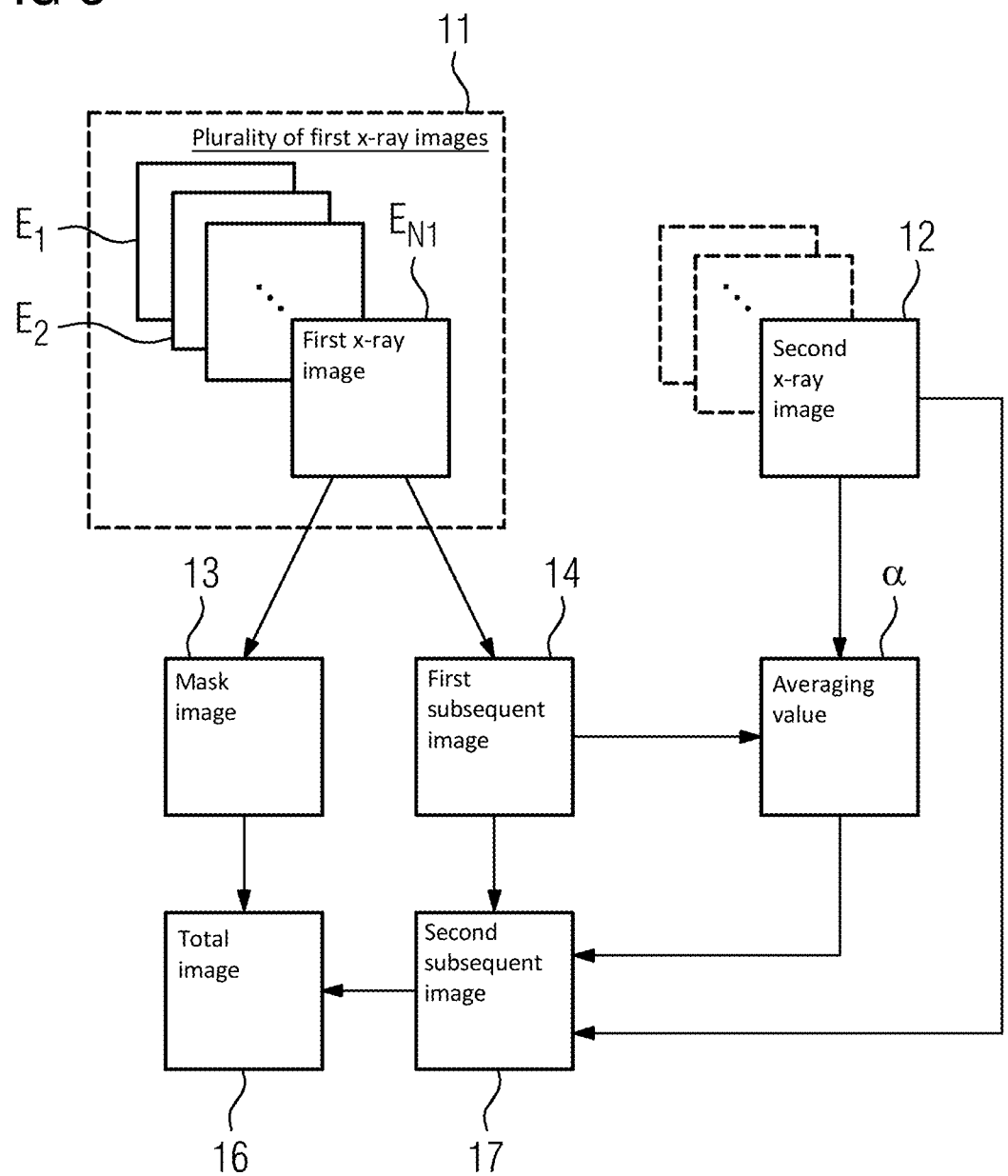
FIG. 3 depicts an example of a schematic representation of the processing acts for generating the images in the individual method acts.

FIG. 3 depicts a schematic representation of the processing acts for generating the images in the individual method acts. Through the averaging of the plurality of first X-ray images 11 recorded in the first act S1 at a constant X-ray imaging frequency and constant X-ray dose for each X-ray image recording, in the second act S2, a mask image 13 is generated. In particular, through the averaging of the plurality of first X-ray images 11 during the generation of the mask image 13, a reduction in the image noise variance and hence an improvement in the image quality may be achieved. This is comparable with an increase in the X-ray dose equivalent of the mask image 13 compared with the X-ray dose equivalent of the individual first X-ray images 11.

Furthermore, from at least one of the plurality of first X-ray images, a first subsequent image 14 may be generated. At least as a function of the at least one second X-ray image 12 recorded in a third act S3, a second subsequent image 17 may be acquired by adaptive averaging with the first subsequent image 14. Here, an averaging value a that is a function of a degree of deviation may be used for the adaptive averaging, wherein the degree of deviation is determined by the deviation between at least one of the first X-ray images 11 and the at least one second X-ray image 12. In the generation of the second subsequent image 17, the first subsequent image 14 and the at least one second X-ray image may be averaged adaptively by the averaging value a. In particular, the averaging value a may be embodied in turn as a weighting image, wherein it is possible as a result thereof for a different weighting to be achieved in the adaptive averaging for each imaging region, e.g., for each pixel. The total image 16 may be generated in a fourth act S4 as a function of the mask image 13 and of the second subsequent image, wherein this may ensue by subtraction. The total image generated in the process may represent a difference image that contains the change over time in the body region of the examination subject 5. In particular, in the generation of the total image 16, an additive linking occurs of the image noise variance from the mask image 13 and from the second subsequent image 17, wherein the image noise variance in the second subsequent image 17 is dependent in turn on the image noise variance in the first subsequent image 14 and on the at least one second X-ray image. In order to not additionally increase the image noise variance in the total image 16 in comparison with the image noise variance in the second subsequent image 17, it may be particularly advantageous to average a higher number of a plurality of first X-ray images to form the mask image 13.

Figure 4:
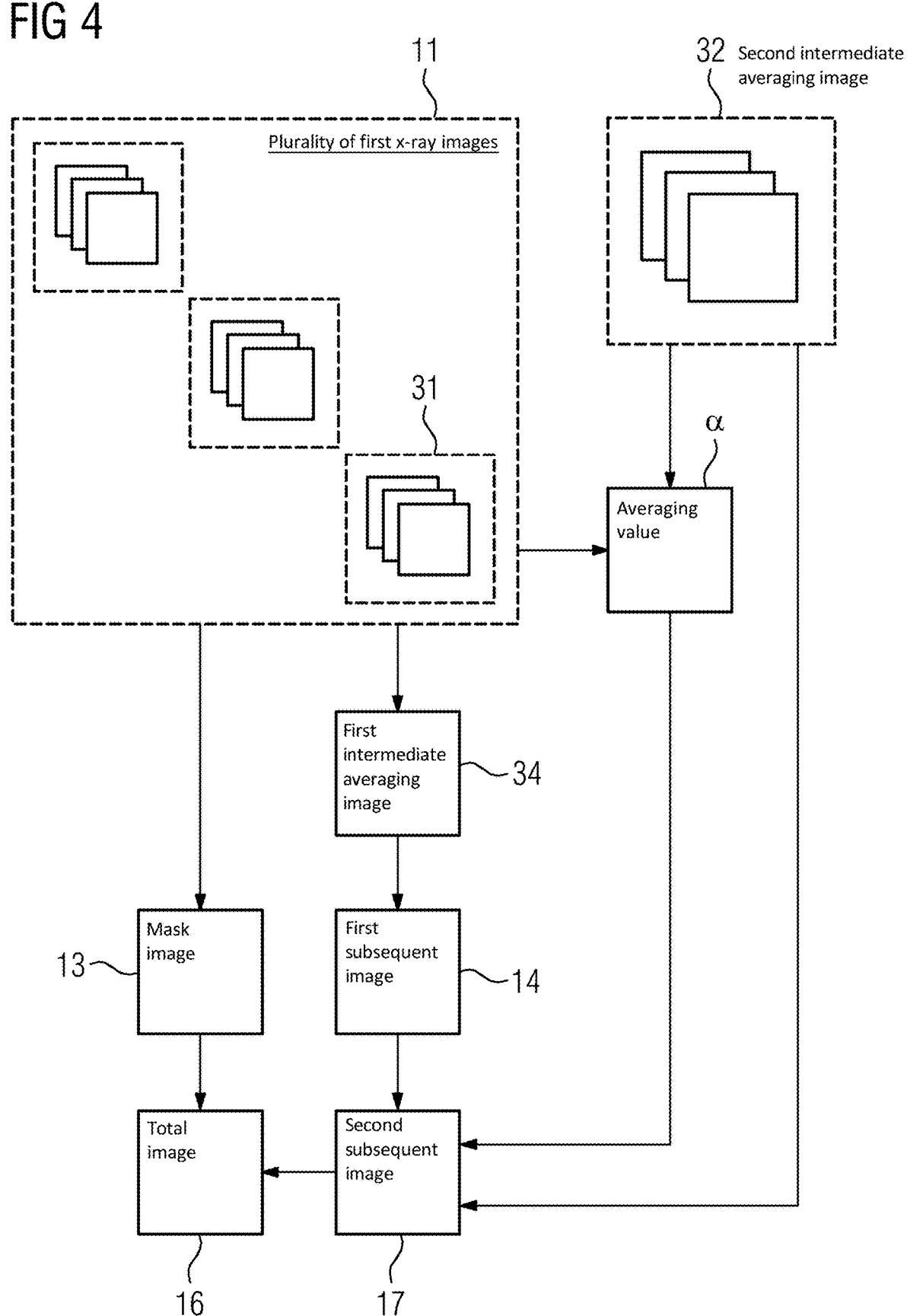
FIG. 4 depicts an example of a schematic representation of the processing acts for generating the images in the individual method acts by an intermediate averaging.

In the embodiment shown in FIG. 4, a plurality of, e.g., a number NZ, of first X-ray images 31 is averaged to form a first intermediate averaging image 34, wherein the first subsequent image 14 is formed from the first intermediate averaging image 34. By the plurality of first X-ray images 11, a mask image 13 is generated.

In particular, the first intermediate averaging image 34 may be averaged from part of the first X-ray images 11, as a result of which the first intermediate averaging image may correspond to a lower X-ray dose equivalent than does the mask image 13. Furthermore, a second intermediate averaging image 32 may be generated by averaging an identical number of second X-ray images as in the generation of the first intermediate averaging image 34. The degree of deviation may be determined by a deviation between the first subsequent image 14 and the second intermediate averaging image 32. The second subsequent image 17 may subsequently be acquired through adaptive averaging of the first subsequent image 14 and of the second intermediate averaging image 32 through an averaging value a that is dependent on the degree of deviation. The first and the second intermediate averaging image may correspond in each case with the same X-ray dose equivalent because, in the respective averaging, an identical number of first and second X-ray images has been averaged in each case. This is facilitated by the fact that the plurality of first and second X-ray images have been recorded at the same constant X-ray imaging frequency and the same constant X-ray dose for each X-ray image recording.

This advantageously facilitates the determination of the degree of deviation by a deviation between the first subsequent image 14, which has been formed from the first intermediate averaging image 34, and the second intermediate averaging image 32. The total image 16 may be generated subsequently as a function of the mask image 13 and of the second subsequent image 17.

In particular, the processing unit 4 is embodied to carry out all the processing acts mentioned in the embodiments. This may include the averaging of a plurality of X-ray images and/or the generation of the mask image 13 and/or the determination of the averaging value a as a function of the degree of deviation and/or the generation of the first subsequent image 14 and of the second subsequent image 17 and/or the generation of the total image 16.

Figure 5:
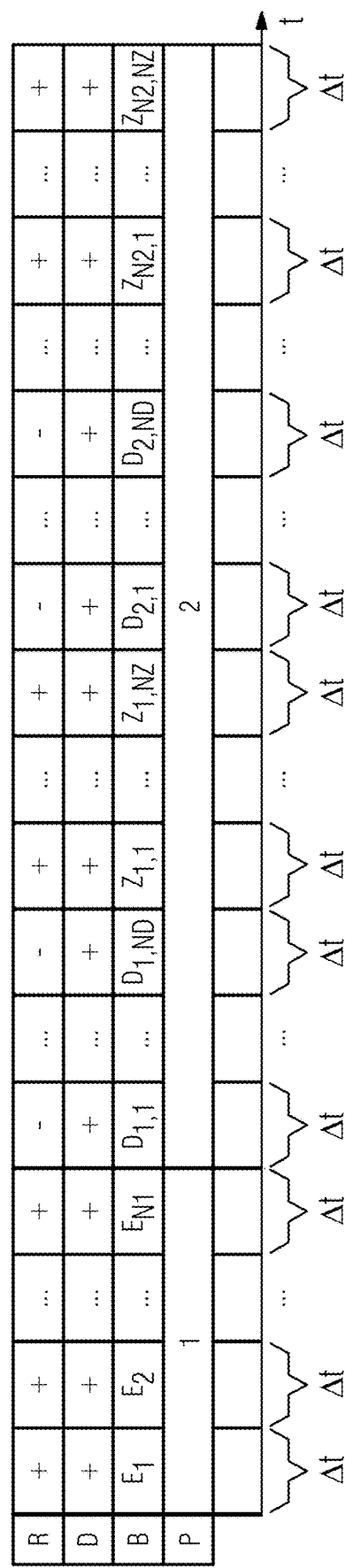
FIG. 5 depicts an example of a schematic flow chart of an X-ray examination for recording a plurality of first and a plurality of second X-ray images.

The time sequence of an X-ray examination for recording a plurality of first and a plurality of second X-ray images is shown schematically in FIG. 5 along a time axis t. The two exemplary phases P of the X-ray examination are marked in FIG. 5 in the last line of the table for the first phase 1 and the second phase 2. In the first line of the table shown in FIG. 5, a status of the X-ray unit R at the times of a recording is shown. Here "+" marks an exposure to X-rays and "−" marks no exposure to X-rays. In the second line of the table shown in FIG. 5, a status of the detector D at the times of a recording is shown. Here "+" marks an X-ray image or dark image recording. The third line of the table shown in FIG. 5 shows which X-ray image or dark image is recorded at which time, for example. In a first phase 1 of the X-ray examination, a plurality of, in particular N1, first X-ray images (denoted by $E_1$, $E_2$ to $E_{N1}$) are recorded. The N1 first X-ray images may be averaged to form the mask image 13. In a chronologically, (e.g., seamlessly), subsequent second phase 2, a plurality of second X-ray images are recorded in the proposed embodiment, wherein prior to at least one of the second X-ray images, a number of ND dark images, (denoted in FIG. 5 by $D_{1,1}$ to $D_{1,ND}$, $D_{2,1}$ to $D_{2,ND}$ and $D_{2,ND}$), are recorded without being illuminated by the X-ray unit 2. For example, after a first recording of ND dark images, $D_{1,1}$ to $D_{1,ND}$, a number of NZ second X-ray images, $Z_{1,1}$ to $Z_{1,NZ}$, are recorded, wherein for recording the second X-ray images, exposure of the detector 3 by the X-ray unit 2 ensues. In particular, in the first phase and in the second phase, measurements may be taken at the same constant X-ray imaging frequency of the detector 3, marked by a constant time interval Δt between the recording of an X-ray image or of a dark image.

Furthermore, an identical number NZ of second X-ray images may be averaged in each case to form a second intermediate averaging image wherein, through the averaging of NZ second X-ray images, a higher X-ray dose equivalent may be achieved in the at least one second intermediate averaging image 32. An identical number NZ of first X-ray images may be averaged to form a first intermediate averaging image 34, as a result of which a direct reconciliation between the first and the at least one second intermediate averaging image 32 is facilitated.

In total, a plurality of dark images and a plurality of second X-ray images may be recorded during the second phase of the X-ray examination, in particular alternately. In particular, N2 second intermediate averaging images, $Z_1, Z_2$ to $Z_{N2}$, may be generated from N2·NZ second X-ray images, $Z_{1,1}$ to $Z_{N2,NZ}$.

Alternatively, N2 second X-ray images may be recorded without any averaging in the second phase of the X-ray examination. Here, a plurality of total images 20 may be generated, each of the plurality of total images 20 being generated by subtraction of the mask image 13. In particular, a number N1 of the plurality of first X-ray images 11 that have been averaged to generate the mask image 13 may be determined through the number N2 of the plurality of second X-ray images.

If, in an exemplary embodiment, N2·NZ second X-ray images are averaged to form in total N2 second intermediate averaging images, the plurality of total images 20 may be generated by subtraction of the mask image 13 from the N2 second intermediate averaging images.

Furthermore, by the recorded dark images $D_{1,1}$ to $D_{1,ND}$, $D_{2,1}$ to $D_{2,ND}$ and $D_{2,ND}$, detector information may be determined, wherein at least one of the plurality of total images 20 is generated taking the detector information into account.

In particular, a plurality of dark images, in particular recorded in chronological sequence, (e.g., a number ND of dark images $D_{1,1}$ to $D_{1,ND}$), may be used to acquire a time sequence of decay characteristics and/or afterglow characteristics of the detector 2 and assign them to the detector information.

Figure 6:
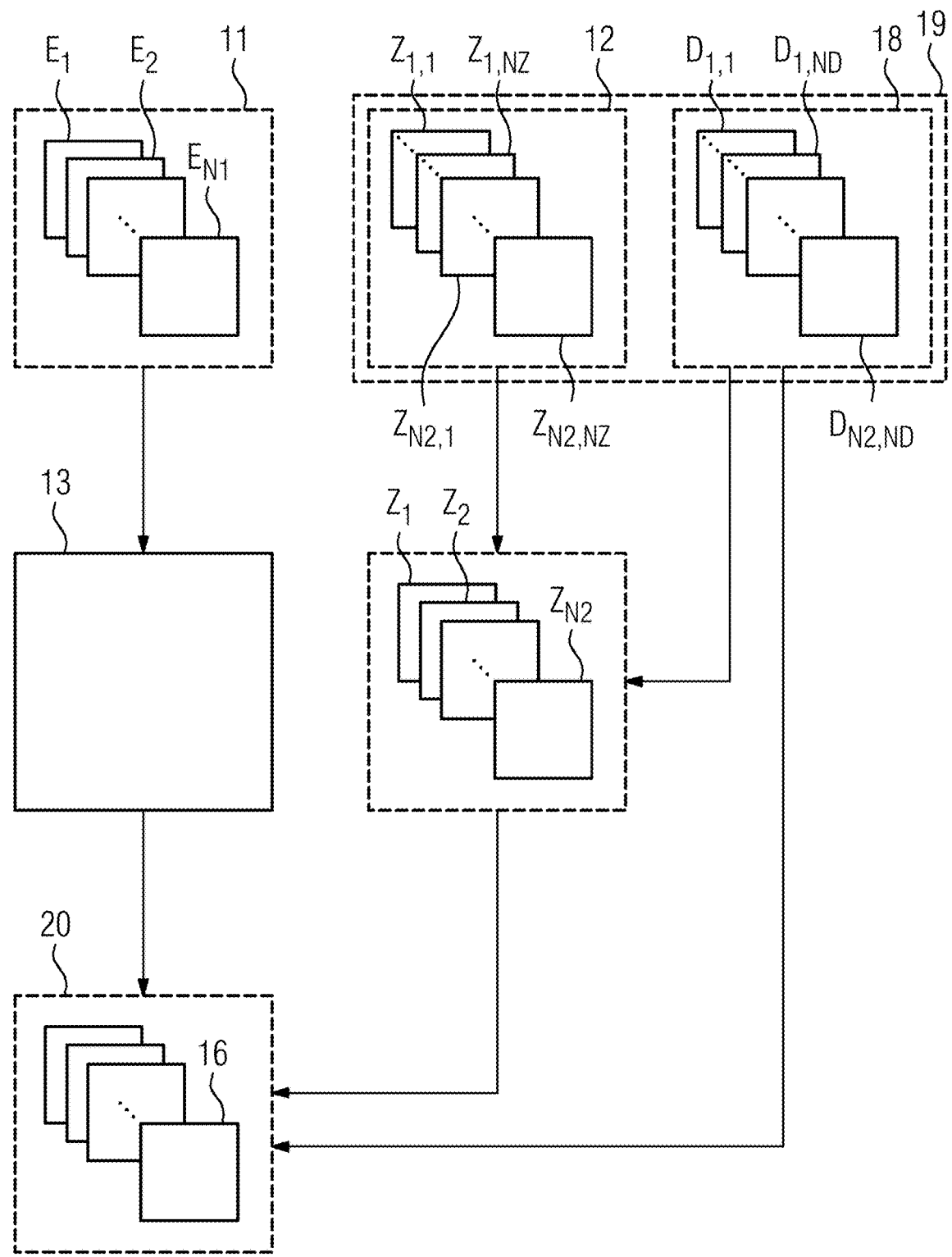
FIG. 6 depicts an example of a schematic representation of the processing acts for generating a plurality of total images.

In the embodiment shown in FIG. 6, a schematic representation of the processing acts for generating a plurality of total images is set out. Here, a plurality of first X-ray images 11, marked by $E_1$, $E_2$ to $E_{N1}$, may be recorded and averaged to form a mask image 13. Furthermore, a plurality of second X-ray images 19 and a plurality of dark images 18 may be recorded. A number of NZ second X-ray images 12 in each case may be averaged to form second intermediate averaging images $Z_1, Z_2$ to $Z_{N2}$. Here, detector information determined by the dark images 18 may be considered. Furthermore, a plurality of total images 20 may be generated, wherein each of the plurality of total images may be generated by subtraction of the mask image 13 from one of the intermediate averaging images $Z_1, Z_2$ to $Z_{N2}$. In particular, detector information determined by the dark images 18 may be considered. The generation of the plurality of total images 20 therefore ensues advantageously as a function of a large number 19 of second X-ray images 19 and dark images 18. In particular, the generation of the plurality of total images 20 may also include a combination of an intermediate averaging process, which includes in each case the averaging of an identical number of first and second X-ray images, and an adaptive averaging process, which includes an adaptive averaging of the first intermediate averaging image 34 and of at least one second intermediate averaging image 32, in particular weighted as a function of an averaging value a.

Furthermore, by the plurality of total images 20, a scene, (e.g., a film and/or a film loop), may be created.

Finally, it is once again pointed out that the detailed methods described in the aforementioned and the X-ray device shown are merely exemplary embodiments that may be varied in very many ways by a person skilled in the art without departing from the scope of the disclosure. Furthermore, the use of the indefinite article "a" or "an" does not preclude the relevant features from being present in plurality. Likewise, the term "unit" does not preclude the relevant components from including a plurality of interacting subcomponents that may optionally also be spatially distributed.

Although the disclosure has been illustrated and described in greater detail by the exemplary embodiments, the disclosure is not restricted by these exemplary embodiments. Other variations may be derived herefrom by the person skilled in the art, without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for operating a medical X-ray device when carrying out an X-ray examination, the method comprising:
   recording a plurality of first X-ray images of a body region of an examination subject, wherein the recording of the plurality of first X-ray images ensues at a constant X-ray imaging frequency and a constant X-ray dose for each X-ray image recording;
   generating a mask image comprising an averaging of the plurality of first X-ray images;
   recording a plurality of second X-ray images of the body region at a time after the recording of the plurality of first X-ray images, wherein the recording of the plurality of second X-ray images ensues at a same constant X-ray imaging frequency and a same constant X-ray dose for each X-ray image recording as for the recording of the first X-ray images; and
   generating a total image at least as a function of the mask image and the plurality of second X-ray images,
   wherein a number of the plurality of first X-ray images that are averaged to generate the mask image is determined through a number of the plurality of second X-ray images.

2. The method of claim 1, wherein, in the generating of the total image, the mask image and at least one second X-ray image of the plurality of second X-ray images are subtracted one from the other.

3. The method of claim 1, wherein the generating of the total image additionally ensues as a function of a second subsequent image,
   wherein a first subsequent image is generated from at least one first X-ray image of the first X-ray images, and
   wherein the second subsequent image is determined by adaptive averaging of the first subsequent image and as a function of at least one second X-ray image of the plurality of second X-ray images.

4. The method of claim 3, wherein the adaptive averaging comprises an averaging of the first subsequent image and the at least one second X-ray image of the plurality of second X-ray images.

5. The method of claim 3, wherein an averaging value dependent on a degree of deviation is determined for the adaptive averaging of the first subsequent image and the at least one second X-ray image of the plurality of second X-ray images, and
   wherein the degree of deviation is determined by a deviation between at least one first X-ray image of the first X-ray images and the at least one second X-ray image of the plurality of second X-ray images.

6. The method of claim 3, wherein an averaging value dependent on a degree of deviation is determined for the adaptive averaging of the first subsequent image and of the at least one second X-ray image of the plurality of second X-ray images, and
   wherein the degree of deviation is determined by a deviation between the first subsequent image and the at least one second X-ray image of the plurality of second X-ray images.

7. The method of claim 3, wherein an averaging value dependent on a degree of deviation is determined,
   wherein a plurality of first X-ray images of the first X-ray images are averaged to form a first intermediate averaging image and an identical number of second X-ray images of the plurality of second X-ray images are averaged to form a second intermediate averaging image,
   wherein the first subsequent image is formed by the first intermediate averaging image,
   wherein the degree of deviation is determined by a deviation between the first subsequent image and the second intermediate averaging image, and
   wherein the adaptive averaging includes averaging of the first subsequent image and of the second intermediate averaging image.

8. The method of claim 3, wherein, in the generating of the total image, the mask image and the second subsequent image are subtracted one from the other.

9. The method of claim 1, wherein only a portion less than all of the first X-ray images are averaged in the generation of the mask image.

10. The method of claim 1,
   wherein a plurality of total images is generated, and
   wherein each total image of the plurality of total images is generated by subtraction of the mask image from one second X-ray image of the plurality of second X-ray images.

11. The method of claim 10, wherein the medical X-ray device comprises an X-ray unit and a detector, and
   wherein after and/or before the recording of at least one second X-ray image of the plurality of second X-ray images, at least one dark image is recorded without exposure of the detector.

12. The method of claim 11, wherein detector information is determined by the at least one dark image, and
   wherein at least one total image of the plurality of total images is generated taking into account the detector information.

13. An X-ray device comprising:
an X-ray unit;
a detector; and
a processor configured to:
- record a plurality of first X-ray images of a body region of an examination subject, wherein the recording of the plurality of first X-ray images ensues at a constant X-ray imaging frequency and a constant X-ray dose for each X-ray image recording;
- generate a mask image comprising an averaging of the plurality of first X-ray images;
- record a plurality of second X-ray images of the body region at a time after the recording of the plurality of first X-ray images, wherein the recording of the plurality of second X-ray images ensues at a same constant X-ray imaging frequency and a same constant X-ray dose for each X-ray image recording as for the recording of the first X-ray images; and
- generate a total image at least as a function of the mask image and of the plurality of second X-ray images,
- wherein a number of the plurality of first X-ray images that are averaged to generate the mask image is determined through a number of the plurality of second X-ray images.

14. A computer program product having program code, wherein the computer program product is configured to be loaded directly into a memory of a processor of an x-ray device, wherein the program code, when executed by the processor, is configured to cause the x-ray device to:
- record a plurality of first X-ray images of a body region of an examination subject, wherein the recording of the plurality of first X-ray images ensues at a constant X-ray imaging frequency and a constant X-ray dose for each X-ray image recording;
- generate a mask image comprising an averaging of the plurality of first X-ray images;
- record a plurality of second X-ray images of the body region at a time after the recording of the plurality of first X-ray images, wherein the recording of the plurality of second X-ray images ensues at a same constant X-ray imaging frequency and a same constant X-ray dose for each X-ray image recording as for the recording of the first X-ray images; and
- generate a total image at least as a function of the mask image and of the plurality of second X-ray images,
- wherein a number of the plurality of first X-ray images that are averaged to generate the mask image is determined through a number of the plurality of second X-ray images.

15. The method of claim 1, wherein the plurality of second X-ray images is recorded following administration of a contrast agent or movement of a catheter.

* * * * *